United States Patent
Hirvonen et al.

(10) Patent No.: US 12,403,327 B2
(45) Date of Patent: Sep. 2, 2025

(54) RADIATION TREATMENT PLANNING SYSTEMS AND METHODS WITH INTERPOLABLE SPOT PLACEMENTS AND DOSE DISTRIBUTIONS

(71) Applicant: Siemens Healthineers International AG, Steinhausen (CH)

(72) Inventors: Petri Hirvonen, Espoo (FI); Pavel Falkovskiy, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 323 days.

(21) Appl. No.: 18/119,238

(22) Filed: Mar. 8, 2023

(65) Prior Publication Data

US 2024/0299773 A1 Sep. 12, 2024

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01)

(58) Field of Classification Search
None
See application file for complete search history.

(56) References Cited

U.S. PATENT DOCUMENTS

| | | | |
|---|---|---|---|
| 2020/0105395 A1 | 4/2020 | Huth et al. | |
| 2020/0129781 A1* | 4/2020 | Engwall | A61N 5/1043 |
| 2021/0101023 A1* | 4/2021 | Abel | A61N 5/1042 |
| 2022/0001203 A1 | 1/2022 | Hirvonen et al. | |
| 2023/0191149 A1 | 6/2023 | Ropo et al. | |
| 2023/0191150 A1 | 6/2023 | Hirvonen et al. | |
| 2023/0405358 A1* | 12/2023 | Lansonneur | A61N 5/1071 |

* cited by examiner

*Primary Examiner* — Hoon K Song
(74) *Attorney, Agent, or Firm* — Harness, Dickey & Pierce, P.L.C.

(57) ABSTRACT

An initial, relatively coarse arrangement of spots in a target volume and a respective dose distribution per spot are accessed from memory or determined. If the dose distributions of neighboring spots do not satisfy a similarity criterion, then a new set of spots with finer spacing is determined for the regions that include dissimilar spots (e.g., spots are added between the dissimilar spots), and spot dose distributions are determined for the new spot arrangement. The process is repeated until the similarity criterion is satisfied for all or a threshold number of spots or until a minimum spot spacing is reached. The final arrangement of spots and dose distributions for the spots can be stored. During subsequent optimization of a treatment plan based on the final arrangement of spots, a dose distribution for a point that is between the spots can be determined by interpolating the dose distributions of nearby spots.

20 Claims, 7 Drawing Sheets

RADIATION TREATMENT PLANNING SYSTEMS AND METHODS WITH INTERPOLABLE SPOT PLACEMENTS AND DOSE DISTRIBUTIONS

BACKGROUND

The use of radiation therapy to treat cancer is well known. Typically, radiation therapy involves directing a beam of radiation (e.g., a high energy proton, photon, ion, neutron, or electron beam) into a target volume (or treatment volume) in the body, such as a malignant tumor, a post-resection tumor bed, a site known to be at risk for tumor progression or a benign lesion, among others.

Radiation therapy using proton beams has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The plan defines various aspects of the radiation therapy using simulations and optimizations that may be based on past experiences. In general, the purpose of the treatment plan is to deliver sufficient radiation to unhealthy tissue while minimizing exposure of surrounding healthy tissue to that radiation.

One type of radiation therapy is known as spot scanning, also known as pencil beam scanning. In spot scanning, a beam is directed to spots in a target volume as prescribed by the treatment plan. The prescribed spot locations are typically arranged in a fixed pattern for each energy layer of the beam, and the beam is delivered on a fixed scanning path within an energy layer. The beams are controlled to conform the radiation dose to the target volume and avoid or reduce exposure of healthy tissue to radiation. For radiation treatment using proton beams, by superposition of several beams of different energies at neighboring spots, the Bragg peaks of the beams will overlap to deliver the prescribed dose across the target volume up to the edges of the volume, with a sharp drop to zero dose beyond the edges.

During treatment planning, a precise determination of the number of spots and their placement (e.g., location and spacing) is critical. The goal is to determine spot placements that: conform to the outline of the target volume, to improve the lateral penumbra and spare healthy tissue outside the target volume from exposure to radiation beyond what is necessary to treat the unhealthy tissue; are uniform inside the treatment volume, to avoid dose variations (dose inhomogeneity) inside the target volume so that the prescribed dose is delivered to all parts of the volume; and minimize the number of spots to the extent possible to reduce the treatment time (dose delivery time) so that treatment is less difficult for the patient.

When generating a treatment plan, an initial arrangement (e.g., pattern of spot placements) is specified for the entire target volume, and the plan is optimized by adjusting the weights of the spots in the pattern. In some instances, a sharper penumbra or more uniform dose distribution could be achieved if the lateral position of the spots could be altered during optimization. However, letting the spot positions vary during optimization of a treatment plan significantly complicates that process.

SUMMARY

In embodiments according to the present disclosure, an initial, relatively coarse arrangement (pattern) of spots in a target volume and a respective dose distribution per spot are accessed from memory or determined (e.g., calculated). In embodiments, the respective spot dose distributions are normalized. For example, the magnitude, range, and width of each spot dose distribution is normalized to determine a normalized value of the spot dose distribution. Normalizing the spot dose distributions reduces the amount of computer system memory needed to store the spot dose distributions and makes evaluating their similarity easier and more robust, among other advantages.

In embodiments, the dose distribution of each spot is compared to the dose distributions of neighboring (e.g., immediately adjacent) spots to determine if the differences between the spot dose distributions satisfies a similarity criterion. As noted, in embodiments, the spot dose distributions are normalized. In addition to the above advantages, the use of normalized values allows the comparisons to be performed faster and reduces the load on processing resources.

If the dose distributions of neighboring spots do not satisfy the similarity criterion, then a new set of spots with a finer spacing (relative to the prior spacing) is determined for the region or sub-volume of the target volume that includes the dissimilar spots. The finer spacing of spots is achieved, for example, by adding spots to the region or sub-volume that includes the dissimilar spots (e.g., by adding spots between the dissimilar spots), thereby increasing the resolution or density of the spots in that region or sub-volume. Dose distributions for the spots in that region or sub-volume are then determined for the new spot arrangement; in embodiments, these spot dose distributions are also normalized.

The process just described is repeated until the similarity criterion is satisfied for a specified number of spots in the target volume (e.g., for all of the spots) or until a minimum spot spacing is reached. When the process is completed, the final arrangement of spots and the (normalized) dose distributions for the spots in the final arrangement can then be stored. In embodiments, that information is stored in a hierarchical, multidimensional data structure such as, but not limited to, a tree structure (e.g., an octree), a lookup table, or an influence matrix.

Generally speaking, as a result of the methods disclosed herein, the final arrangement of spots, and hence the data structure, will have a higher resolution (more spots) where the stopping power of the target volume is more heterogeneous and a lower resolution (less spots) where the stopping power is more homogeneous. This can reduce storage requirements and make the data structure more practical.

For example, during optimization of a treatment plan based on the final arrangement of spots, a dose distribution for a point (e.g., a voxel) that is between the spots can be determined by interpolating the dose distributions of nearby spots using the information stored in the data structure. This feature allows the influence of spots on a nearby voxel to be determined quickly, which can be especially useful for fast optimizations. Normalizing the spot distributions makes it easier to interpolate them. The optimization process can also be run simultaneously or asynchronously with the calculation of the information being stored in the data structure, by using the information for the coarsest arrangement of spots first and then using the information for the finer arrangements of spots as that information becomes available.

These and other objects and advantages of embodiments according to the present disclosure will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments according to the present disclosure and, together with the detailed description, serve to explain the principles of the disclosure. The drawings are not necessarily drawn to scale.

DETAILED DESCRIPTION

Figure 1:
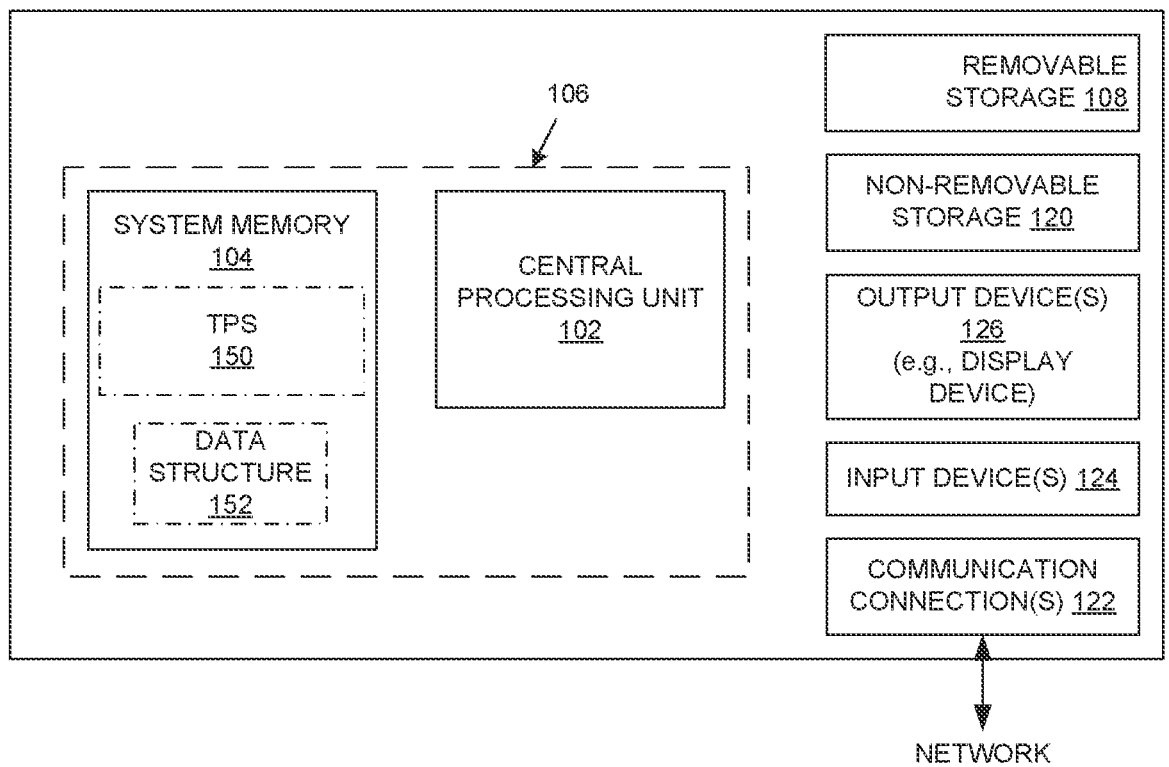
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "determining," "storing," "optimizing," "generating," "evaluating," "using," "selecting," "identifying," "increasing," "normalizing," "interpolating," or the like, refer to actions and processes (e.g., the flowcharts of FIGS. 8 and 9) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

Portions of the detailed description that follows are presented and discussed in terms of methods or processes. Although operations and sequencing thereof are disclosed herein, such operations and sequencing are examples only. Embodiments are well-suited to performing various other operations or variations of the operations described herein.

Embodiments described herein may also be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EEPROM), flash memory or other memory technology, compact disk ROM (CD-ROM), digital versatile disks (DVDs) or other optical or magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

The discussion to follow may include terms such as "dose," "dose rate," etc. Unless otherwise noted, a value is associated with each such term. For example, a dose has a value and can have different values. For simplicity, each of these terms means its value, unless otherwise noted or apparent from the discussion.

Embodiments according to the present disclosure can be used for radiation therapy/treatment modalities including but not limited to enhanced dose rate (EDR) radiation therapy (RT), ultra-high dose rate (UHDR) RT, and FLASH RT. EDR is defined as a dose rate ranging from one to 40 grays per second (Gy/s). UHDR is defined as a dose rate greater than 40 Gy/s. FLASH RT is a special case of UHDR RT, where in addition to the dose rate, the expected tolerance of the healthy tissue is greater than that expected from low dose rates, due to the so-called "FLASH effect." In particular, embodiments according to the present disclosure include combinations of spatially fractionated radiation therapy (SFRT) including, but not limited to, EDR RT, UHDR RT, FLASH RT. Embodiments according to the present disclosure are applicable to radiation therapy that uses any form of radiation including, but not limited to, protons, photons, ions, neutrons, or electrons. Embodiments according to the present disclosure are also applicable to intensity modulated radiation therapy (IMRT) and intensity modulated particle therapy (IMPT).

The methodologies disclosed herein may also be useful for stereotactic radiosurgery as well as stereotactic body radiotherapy with single or multiple metastases.

Introduction

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as a keyboard, mouse, pen, voice input device, touch input device, etc. Output device(s) 126 such as a display device, speakers, printer, etc., may also be included. A display device may be, for example, a cathode ray tube display, a light-emitting diode display, or a liquid crystal display.

In the example of FIG. 1, the memory 104 includes computer-readable instructions, data structures (e.g., the data structure 152), program modules, and the like associated with a treatment planning system (TPS) 150, which may also be referred to as an optimizer. However, the TPS 150 may instead reside in any one of the computer storage media used by the computer system 100, or may be distributed over some combination of the computer storage media, or may be distributed over some combination of networked computers. The TPS 150 is used to generate and evaluate candidate (proposed) treatment plans and produce a final (optimized) treatment plan. A candidate radiation treatment plan is defined using the TPS 150, stored in a computer system memory, and accessed from that memory.

Figure 4:
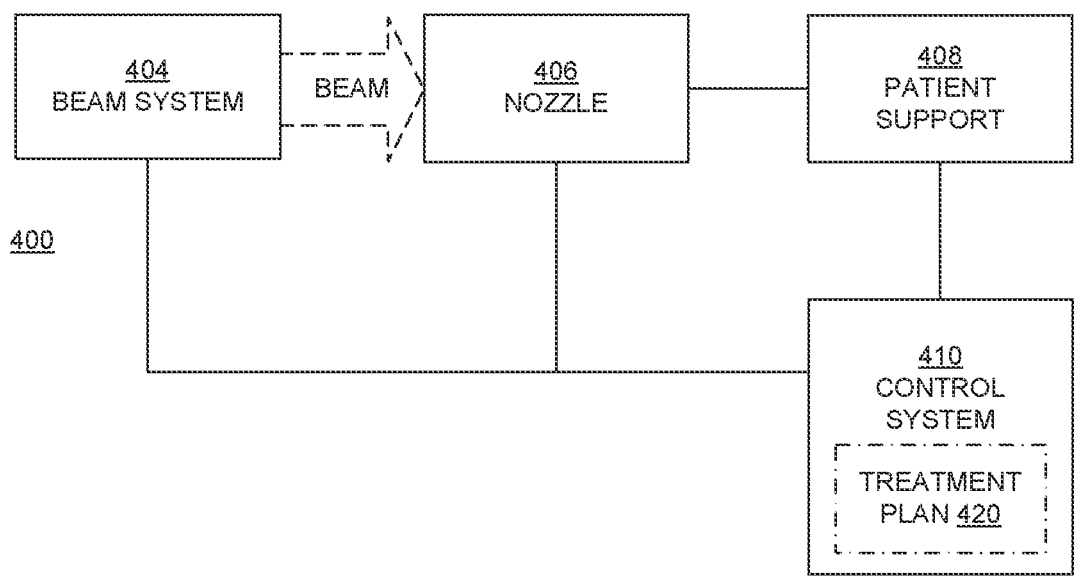
FIG. 4 is a block diagram showing selected components of a radiation therapy system upon which embodiments according to the present disclosure can be implemented.

To deliver the prescribed dose/dose rate of radiation, the radiation treatment plan can be converted (e.g., by the TPS 150) into machine parameters used to configure and control a treatment system (e.g., the system 400 of FIG. 4). Depending on the type of treatment, the machine parameters can include, but are not limited to, beam currents of charged particles, ions, or photon beam intensities, the number of charged particles, ions, or photons per time segment to be emitted by the accelerator, magnet currents, settings to achieve the prescribed energy of beam "particles" (e.g., protons, photons, ions, neutrons, or electrons) at the target volume, and the measurement range of a dose monitor system.

During treatment, in an example embodiment, a beam enters a nozzle of a treatment machine, which may include one or more components that affect (e.g., decrease, modulate) the energy of the beam, to control the dose/dose rate delivered by the beam and/or to control the dose versus depth curve of the beam, depending on the type of beam. For example, for a beam that has a Bragg Peak, the nozzle can control the location of the Bragg Peak in the target volume laterally to the beam axis.

In embodiments according to the disclosure, the nozzle emits particles in a spot scanning beam (also referred to as a pencil beam). The nozzle is mounted on a moveable gantry so that the beam can be delivered from different directions (angles) relative to a patient on the patient support device, and the position of the patient support device relative to the beam may also be changed. The target volume is irradiated with a raster scan by the spot scanning beam.

The beam can deliver a relatively high dose rate (a relatively high dose in a relatively short period of time). For example, if necessary, the beam can deliver at least 40 Gy in less than one second, and may deliver as much as 120 Gy per second or more.

Examples of Automated Radiation Treatment Planning Processes

A candidate or proposed radiation treatment plan includes values of parameters that can affect dose and/or dose rate, as well as other parameters. The parameters depend on the treatment modality.

The parameters may include, but are not limited to: treatment field (the regions in a patient that will receive radiation); beam shape; beam collimation; number and arrangement of spots; spot weights; beam weights; beam intensities or energies; beam directions; prescribed dose and prescribed dose rate; a number of irradiations of a target volume; a duration of each of the irradiations (irradiation times); and a dose deposited in each of the irradiations. The parameters may also include a period of time during which the irradiations are applied (e.g., a number of irradiations are applied over a period of time such as an hour, with each irradiation in the period of time separated from the next by another period of time; while a treatment session may be relatively long, individual beam delivery times may be less than, even much less than, a second) and an interval of time between each period of irradiations (e.g., each hour-long period is separated from the next by a day).

The large number of parameters and their ranges of values can lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

Because of the different parameters that need to be considered, the range of values for those parameters, the interrelationship of those parameters, the need for treatment plans to be effective yet minimize risk to the patient, and the need to generate high-quality treatment plans quickly, the use of the treatment planning system 150 executing consistently on the computer system 100 (FIG. 1) for radiation treatment planning as disclosed herein is important.

Figure 2:
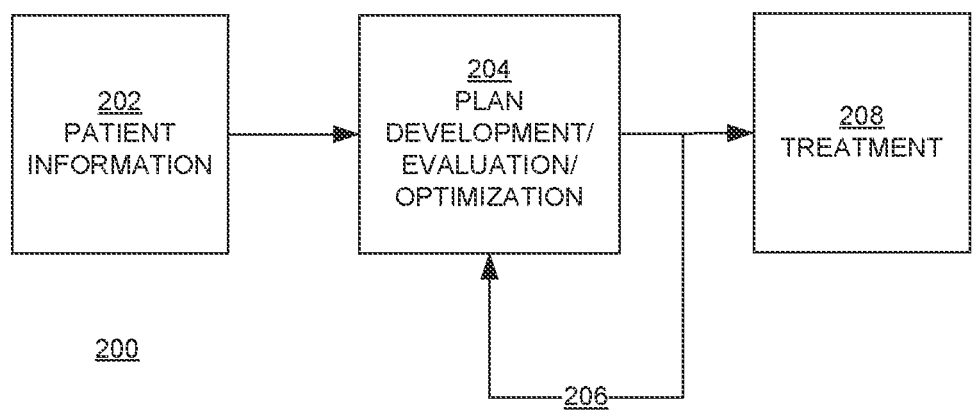
FIG. 2 is a block diagram illustrating an example of an automated radiation therapy treatment planning process in embodiments according to the present disclosure.

FIG. 2 is a block diagram illustrating an example of an automated radiation therapy treatment planning process 200 in embodiments according to the present disclosure. The process 200, in whole or in part, may be implemented as a software program, hardware logic, or a combination thereof on/using the computer system 100 (FIG. 1).

In block 202 of FIG. 2, three-dimensional (3D) images of a patient are obtained, and organs and other structures in the patient (the patient geometry) can be segmented and contoured. In blocks 204 and 206, the information from block 202, and other information such as that mentioned above, are used to develop and evaluate a candidate treatment plan, as described further below in conjunction with FIG. 3.

In block 208, if the candidate treatment plan is satisfactory (e.g., it satisfies clinical goals), then the plan may be used for treatment of the patient. If not, then aspects of the treatment plan and/or of the clinical goals may be modified iteratively until a satisfactory plan is generated. The clinical goals may be expressed in terms of, for example, a set of quality metrics, such as dose uniformity in the target volume, conformity to the target volume, critical organ sparing, and the like, with respective target or threshold values for the quality metrics.

In practice, the clinical goals may conflict with each other, in the sense that not all of the clinical goals can be satisfied by any particular treatment plan. Where clinical goals conflict, some or all of the parameter values for each candidate radiation treatment plan can be iteratively adjusted to determine a final set of parameter values for each plan that results in a plan that satisfies the objectives (clinical goals) for treatment of the patient and minimizes the total objective function for that plan. For instance, a dose prediction model (e.g., an element of the TPS 150 of FIG. 1) can be used to generate alternative outcomes for various combinations of the adjustable parameters, and a total objective function can be computed for various alternative outcomes until a minimum or satisfactory value is found, as described further below.

Figure 3:
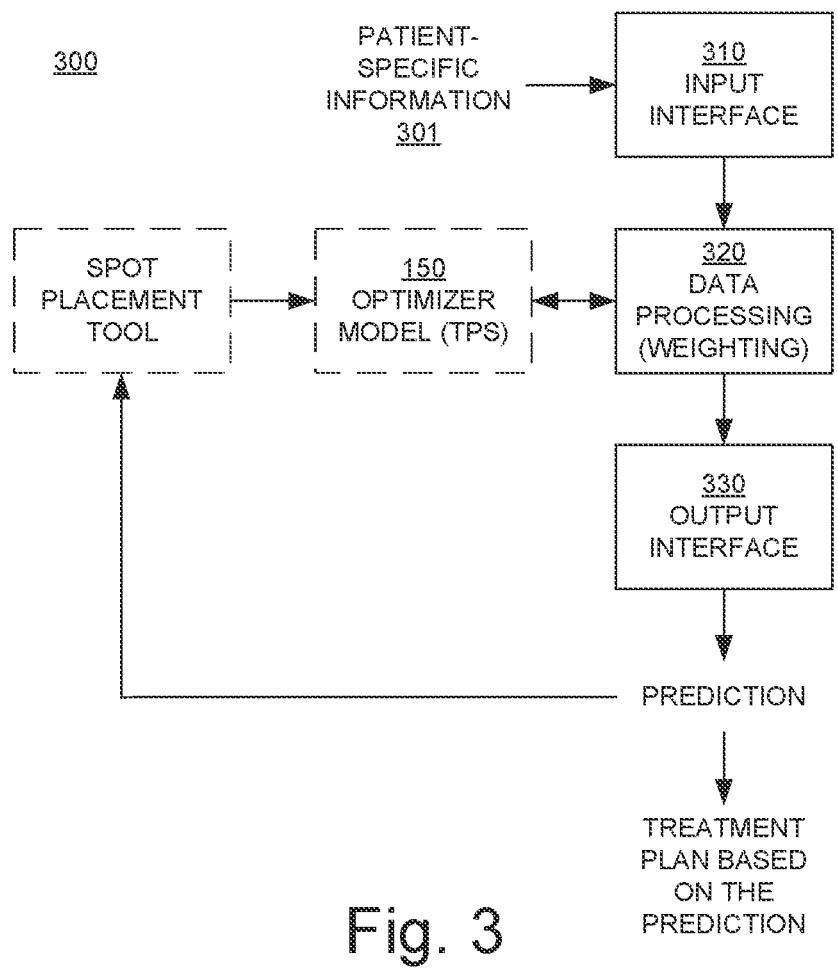
FIG. 3 is a block diagram illustrating an example of an automated radiation therapy treatment planning system in embodiments according to the present disclosure.

FIG. 3 is a block diagram illustrating an example of an automated radiation therapy treatment planning system 300 in embodiments according to the present invention. The system 300 includes an input interface 310 to receive patient-specific information (e.g., data) 301, a data processing component 320 that implements the treatment planning system 150, and an output interface 330. The system 300 in whole or in part may be implemented as a software program, hardware logic, or a combination thereof on/using the computer system 100 (FIG. 1).

In the example of FIG. 3, the TPS 150 accesses or receives (e.g., from the memory 104 of FIG. 1) information that includes parameters such as those mentioned above. The TPS 150 can also access or receive information 301 specific to the patient to be treated (e.g., patient geometry), including information that describes a treatment or target volume (or region of interest, ROI), which can include a planned target volume (PTV), gross tumor volume (GTV), clinical target volume (CTV), and organs-at-risk (OARs).

In the example of FIG. 3, the patient-specific information 301 is provided to and processed by the treatment planning system 150, which yields a prediction result. A proposed radiation treatment plan based on the prediction result can then be generated.

The inputs to the data processing component 320 (e.g., the treatment planning system 150) include an initial arrangement (or pattern or grid or placement) of spots in the treatment target. The initial spot arrangement may itself be generated by a spot placement tool that is coupled to or is a component of the treatment planning system 150.

As will be described further below, in embodiments according to the present disclosure, the initial spot arrangement for optimization in the treatment planning system 150 considers or is based on the size and/or shape of the treatment target. The treatment planning system 150 can then adjust the locations, number, and weights of spots. The goal is to determine an arrangement of spots and set of spot weights so that, during treatment, the treatment target will receive a homogenous dose (a uniform dose across the treatment target or target volume) and the delivered dose will conform more closely to the edges of the treatment target or volume.

More specifically, the proposed radiation treatment plan is evaluated to determine whether or not objectives (e.g., clinical goals) that are specified for treatment of a patient are satisfied by the proposed radiation treatment plan. The clinical goals or objectives may be expressed in terms of a set of quality metrics, such as target homogeneity, conformity to the treatment target, critical organ sparing, and the like, with respective target values for the metrics.

If the treatment planning system 150 is unable to converge on an arrangement of spots that satisfy those goals, then the initial spot pattern can be changed and the process just described can be repeated. Several satisfactory treatment plans may be determined, in which case the treatment plan that is judged as best satisfying the specified objectives (clinical goals) can be selected as the prescribed (final) treatment plan.

The TPS 150 also accesses or receives objective function formulations (or cost functions) that are defined for the treatment of the patient. Objective function formulations are mathematical formulations of variables (parameters such as those mentioned above) that can have an effect on achieving the clinical goals. More specifically, the objective function formulations are used to evaluate candidate radiation treatment plans, to determine whether or not the clinical goals that are specified for treatment of a patient are satisfied.

In embodiments, the goal is to minimize the value of each objective function formulation. However, in practice, there may be several objective function formulations that are to be minimized in order to achieve an optimal final treatment plan. The objective function formulations may conflict with each other; that is, minimizing the value of one objective function formulation may penalize (e.g., increase) the value of another objective function formulation, and so minimizing the values of all of the objective function formulations may not be achievable. Thus, in embodiments, the objective function formulations are weighted and summed to provide a total of all of the objective function formulations, and that total is then minimized.

In embodiments, a candidate treatment plan that yields a value for the total objective function that is closest to the minimum (relative to other proposed plans) can be identified as an optimized treatment plan. Information about the optimized treatment plan can be presented to the user (e.g., in a display). A planner can iterate on the planning process, e.g., by adjusting the clinical goals. Once a final optimized treatment plan is determined, adjustable treatment machine parameters corresponding to the final optimized treatment plan can be provided in machine-readable form to the radiation treatment system, which can then be operated in accordance with the plan to deliver radiation treatment to a patient.

Example Treatment System

FIG. 4 is a block diagram showing selected components of a radiation therapy or treatment system 400 upon which embodiments according to the present disclosure can be implemented. In the example of FIG. 4, the system 400 includes a beam system 404 and a nozzle 406.

The beam system 404 generates and transports a beam. In embodiments, depending on the type of beam, the beam system 404 includes components that direct (e.g., bend, steer, focus, or guide) the beam in a direction toward and into a nozzle 406. The beam system 404 may also include components that are used to adjust (e.g., reduce or modulate) the beam energy entering the nozzle 406. The nozzle 406 is used to aim or direct the beam toward various locations or spots in a target volume within a patient supported on the patient support device 408 (e.g., a chair or table) in a treatment room. The nozzle 406 may be mounted on or a part of a gantry that can be moved relative to the patient support device 408, which may also be moveable. The nozzle 406 may also include components that direct the beam and/or adjust the beam energy.

The control system 410 implements a prescribed or optimized or final radiation treatment plan 420 received from the TPS 150 (e.g., see FIG. 1). In embodiments, the control system 410 includes a computer system having a processor, memory, an input device (e.g., a keyboard), and perhaps a display, similar to the system 100 of FIG. 1. The control system 410 can receive data regarding operation of the system 400. The memory of the control system 410 stores the radiation treatment plan 420 that will be implemented using the system 400. Specifically, the memory of the control system 410 includes computer-readable instructions, data structures, program modules, and the like associated with the radiation treatment plan 420. The control system 410 can control parameters of the beam system 404, nozzle 406, and patient support device 408, including parameters such as the energy, intensity, direction, size, and/or shape of the beam, according to data it receives and according to the radiation treatment plan 420.

Optimizing and Storing an Arrangement of Spots and Per-Spot Dose Distributions

In overview, embodiments according to the present disclosure introduce methods and systems for forming a multiscale (e.g., three-dimensional) data structure (e.g., an influence matrix, tree structure, or lookup table) that can be formed quickly and that reduces the typically large storage requirements of such data structures. Embodiments according to the present disclosure also introduce methods and systems for utilizing the data structure during treatment planning. For example, the information in the data structure can be interpolated to allow efficient optimization of both spot weights and spot locations during radiation treatment planning.

In the disclosed embodiments, a relatively coarse arrangement of spots and associated spot dose distributions are initialized in a target volume, and that arrangement is recursively refined and stored in the data structure until the dose distributions of neighboring spots are similar enough to satisfy a specified similarity criterion. During dose optimization, the dose distributions of additional spots or voxels can be interpolated using the information in the data structure. For example, for a given beam/field angle, the influence of an arbitrary spot (with arbitrary lateral position and arbitrary energy) on a voxel can be interpolated using the information in the data structure.

In addition, as a consequence of performing the disclosed methods, the information in the data structure has a coarser resolution for more uniform (homogeneous) regions of the target volume and a finer resolution for more heterogeneous regions of the target volume. Thus, in total, the number of spots can be reduced, also reducing the number of dose calculations, all of which means faster calculations and optimizations of treatment plans and reduced storage requirements.

In embodiments according to the present disclosure, an initial, relatively coarse arrangement of spots in a target volume and a respective dose distribution per spot are accessed from computer system memory, or they are determined (e.g., calculated) for each field (beam). The location of each spot, and a dose distribution for each spot, are then stored in computer system memory in the aforementioned data structure (e.g., the data structure 152 of FIG. 1).

The initial arrangement of spots can be a rectilinear grid, but different or more elaborate arrangements can be used as the initial arrangement. For instance, a knowledge database of past treatment plans can be accessed and used to select or determine an initial arrangement that is more elaborate than a simple grid pattern.

Spot locations and spot dose distributions depend on, for example, the angles of the beams and their directions, and also on the energy of each beam as a function of depth in the target volume (the latter of which is also a function of the stopping powers of the media or tissue that the beam passes through). In an embodiment, the spot locations are defined in units of the lateral angle and energy of a beam.

In embodiments, the respective dose distributions per spot are each normalized. For example, the magnitude, range, and width of the dose distribution for each spot is normalized to determine a normalized value of the dose distribution, and mathematical translations and rotations can be eliminated. In those embodiments, the location of each spot and the normalized dose distribution for each spot are then stored in computer system memory in the data structure 152.

Normalizing the dose distributions reduces the amount of computer system memory needed to store the data structure. In embodiments, the normalized values are truncated at a specified dose threshold; this can result in instances in which a truncated normalized value is equal to zero, thereby further reducing the amount of memory needed to store the data structure. Another option for reducing the size of the data structure is to store values for only a certain number of principal spots; for example, one spot can be used to represent other spots (e.g., neighboring spots) that have the same or a similar dose distribution.

Normalizing the spot dose distributions also makes evaluating their similarity easier and more robust. By normalizing the spot dose distributions, it is easier to compare dose distributions of neighboring spots to determine the difference in dose distributions between neighboring spots, which is significant for determining the number and locations of spots as will be described further below, and which in turn is significant for achieving a uniform dose distribution across the target volume.

As noted above, the data structure 152 includes spot locations and a dose distribution per spot. In embodiments, using the information in the data structure 152, the dose distribution of each spot is compared to the dose distributions of neighboring (e.g., immediately adjacent) spots to determine if the differences between the dose distributions satisfy a similarity criterion. Also as noted, in embodiments, the spot dose distributions are normalized. The use of normalized values allows the comparisons to be performed faster and reduces the load on processing resources. The similarity of normalized dose distributions between spots can be determined by comparing their maximum pointwise absolute difference to an epsilon value. A gamma comparison or other various norms of measuring their differences can also be used. A machine learning model such as a neural network can also be used for the similarity evaluation.

Figure 5:
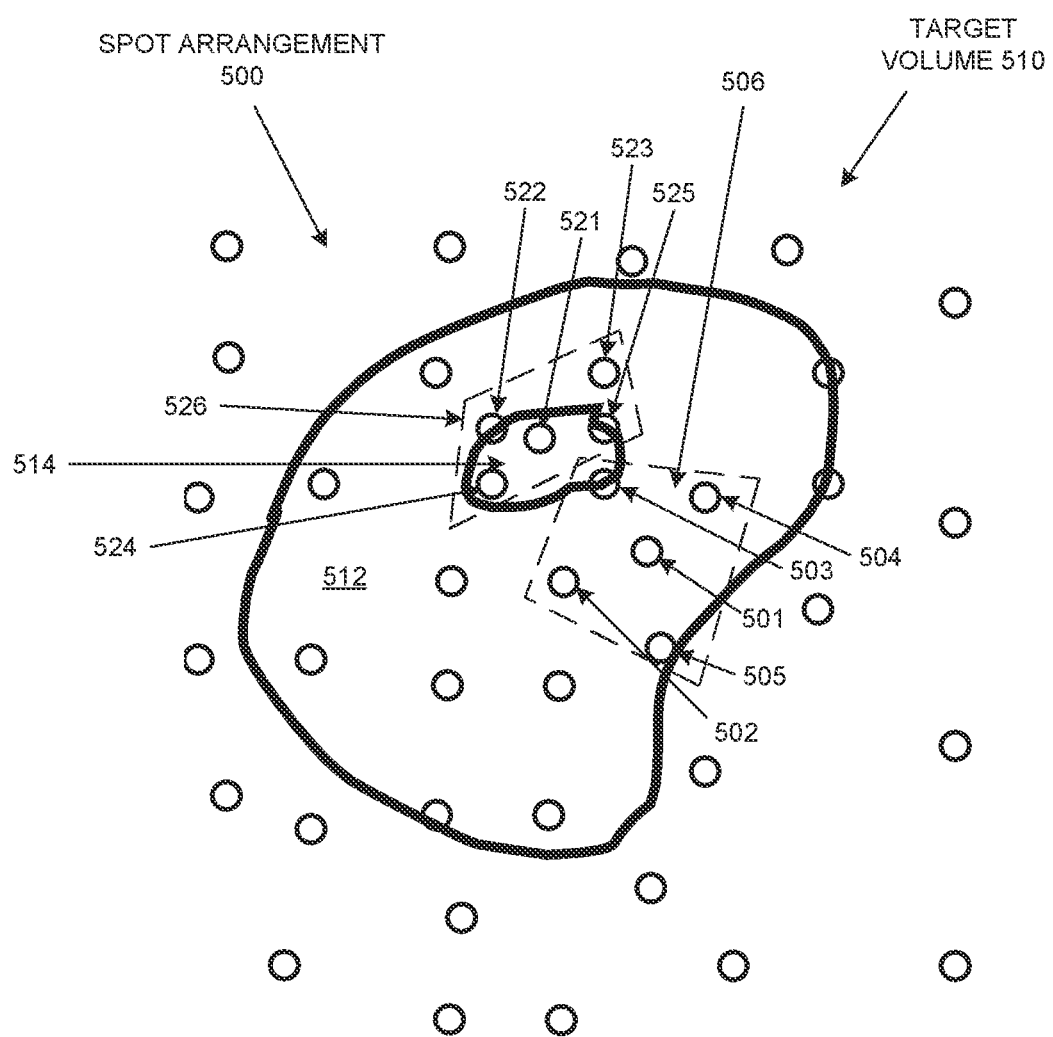
FIGS. 5, 6, and 7 illustrate examples of arrangements of spots at different stages during execution of a method for radiation treatment planning in embodiments according to the present disclosure.
Figure 6:
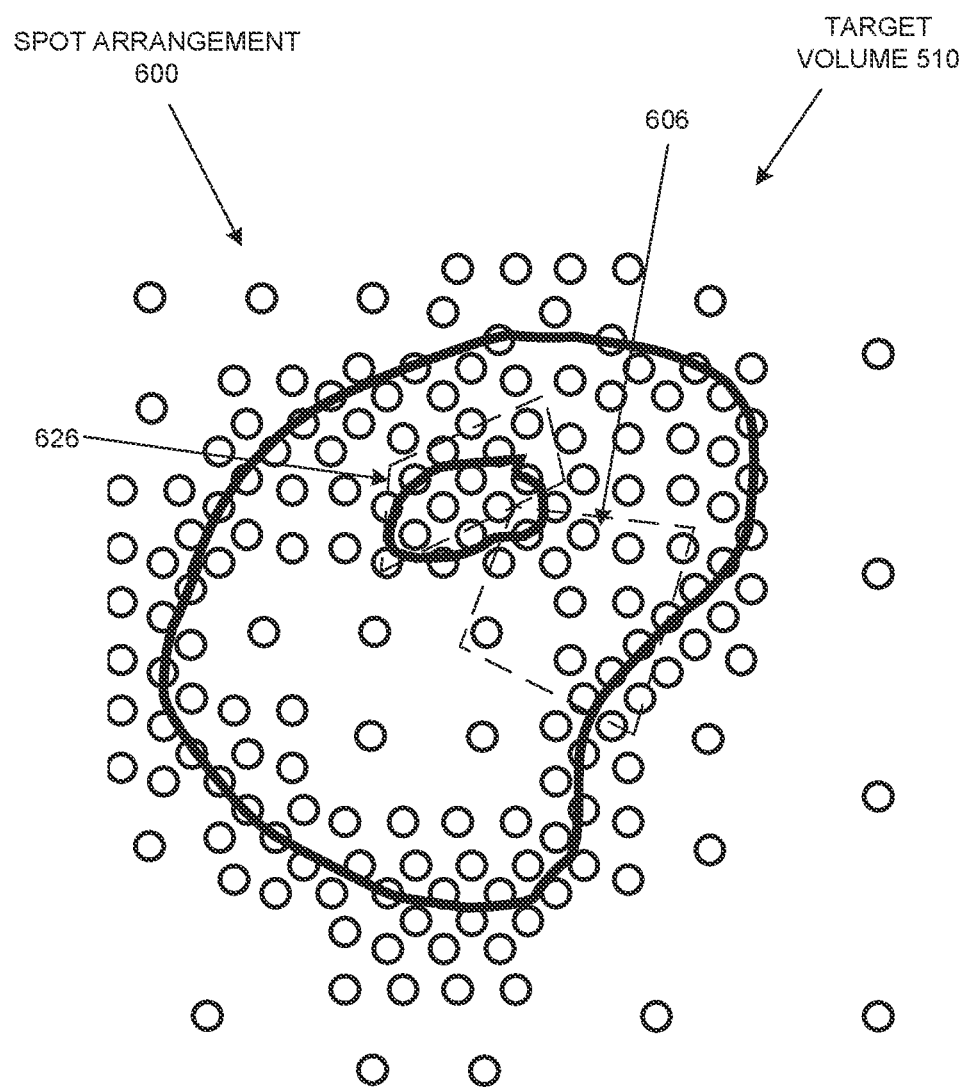

If the dose distributions of neighboring spots do not satisfy the similarity criterion, then a new set of spots with a finer spacing (relative to the prior spacing) is determined for each region or sub-volume of the target volume defined by (encompassing) the set of dissimilar spots (see FIGS. 5 and 6 and the associated discussion). The finer spacing of spots (relative to the prior spacing) is achieved, for example, by adding new spots to each region or sub-volume that includes the set of dissimilar spots (e.g., by adding new spots between the dissimilar spots), thereby increasing the resolution or density of the spots in these regions or sub-volumes. Dose distributions for the spots in that region or sub-volume are then determined; in embodiments, these dose distributions are also normalized. Note it is not necessary to determine (recalculate) spot dose distributions in regions or sub-volumes of the target volume where spots were not added.

The data structure 152 (FIG. 1) is then updated to reflect the most recent arrangement of spots. Note it is necessary for the update to only include the new (added) spot locations and the associated (normalized) dose distribution associated with those spots. Updating only a portion of the data structure allows the update to be performed more quickly, thus consuming less computer system resources.

The process just described is repeated until the similarity criterion is satisfied for a specified number of spots in the target volume (e.g., for all of the spots, or for a threshold number of spots that is less than all of the spots) or until a minimum spot spacing is reached. The dose calculations are performed at the same resolution and to the same precision at each step of the process. When the process is completed, the data structure will include the final arrangement (locations) of spots and the (normalized) dose distributions for the spots in the final arrangement. As described above, the size of the final data structure can be reduced by truncating values or by storing information only for selected spots.

Generally speaking, as a result of the methods disclosed herein, the final arrangement of spots, and hence the data structure, will have a higher resolution (more spots) where the stopping power of the target volume is more heterogeneous and a lower resolution (less spots) where the stopping power is more homogeneous. This can reduce storage requirements and make the data structure more practical. Also, spot positions can be varied during optimization of a treatment plan in a relatively simple and straight-forward manner in a manner that is less complicated than conventional optimization processes.

For example, during optimization of a treatment plan based on the final arrangement of spots, a dose distribution for a point (e.g., a voxel) that is between the spots can be determined by interpolating the dose distributions of nearby spots using the information stored in the data structure. This feature allows the influence of spots on a nearby voxel to be determined quickly, which can be especially useful for fast optimizations.

The optimization process can also be run simultaneously or asynchronously with the calculation of the information being stored in the data structure, by using the information for the coarsest arrangement of spots first and then using the information for the finer arrangements of spots as that information becomes available.

Figure 7:
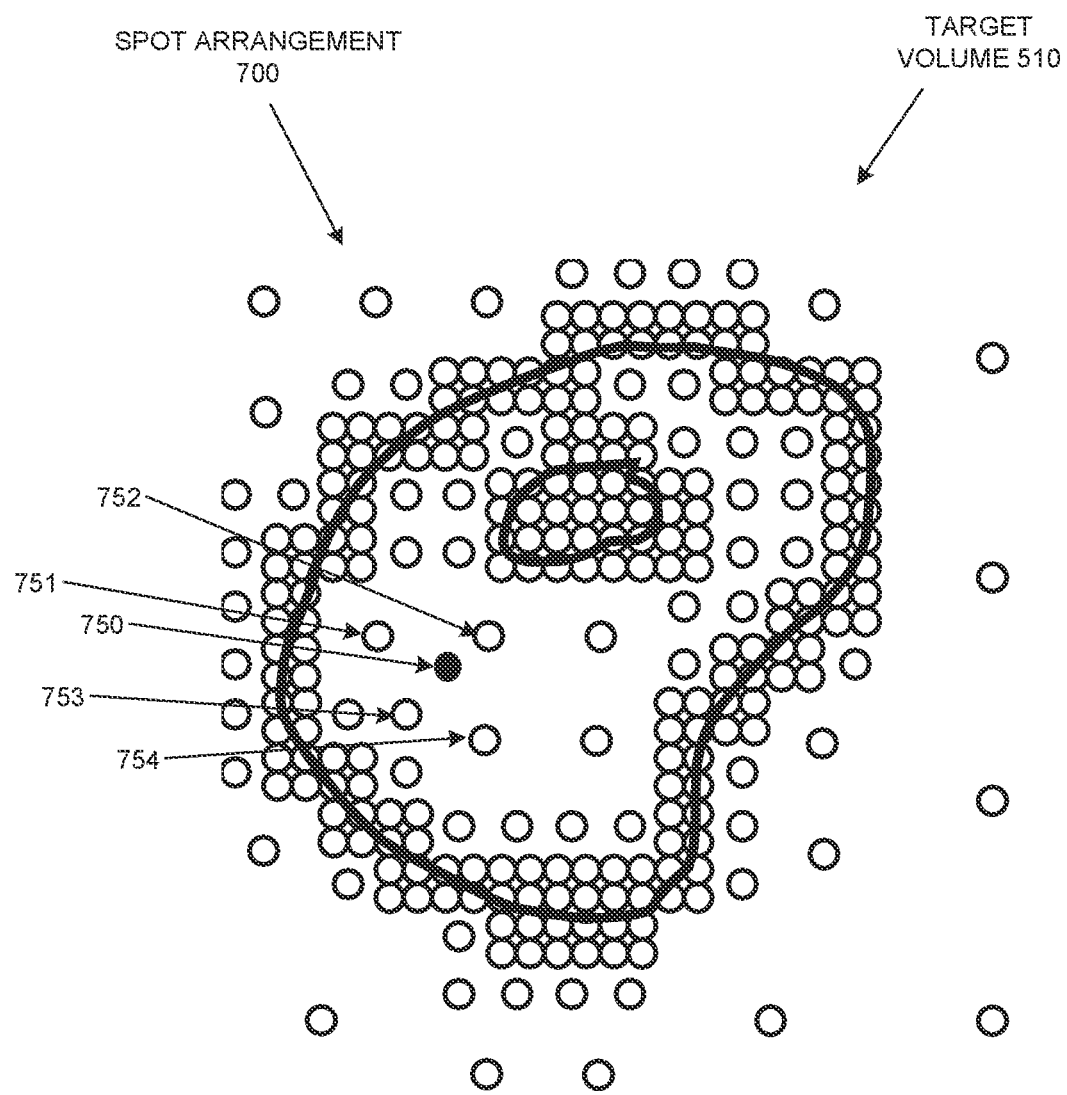

The methodology just described is illustrated in FIGS. 5, 6, and 7, which illustrate examples of arrangements of spots at different stages during execution of that methodology. While only three stages or steps are illustrated and described, the illustrations and description can be readily extrapolated to any number of stages.

FIGS. 5, 6, and 7 illustrate an example of a representation of a cross-section of a target volume 510 in a patient that is modeled according to embodiments in accordance with the present disclosure. In those examples, the target volume 510 is logically or virtually segmented into segmented regions or sub-volumes 512 and 514. For example, the stopping power of the segmented region 512 may be more homogeneous, while the stopping power of the segmented region 514 may be more heterogeneous. In embodiments, the target volume 510 is segmented in this manner using an automatic segmentation tool. Alternatively, the target volume 510 can be segmented by a clinician.

While the examples of FIGS. 5, 6, and 7 include two segmented regions, the present disclosure is not so limited. Also, FIGS. 5, 6, and 7 show arrangements of spots that are rectilinear in spatial coordinates; however, the present disclosure is not so limited. For example, an arrangement of spots that is rectilinear in terms of lateral beam angle and energy (e.g., a divergent grid with warped energy layers) can be implemented.

FIG. 5 includes an initial arrangement 500 of spots, exemplified by the spots 501, 502, 503, 504, and 505 (501-505) and the spots 521, 522, 523, 524, and 525 (521-525). For the purposes of this discussion, the set of spots 501-505 can themselves be viewed as constituting a region or sub-volume 506, and the set of spots 521-525 can themselves be viewed as constituting a region or sub-volume 526. The regions 506 and 526 are not necessarily aligned with the segmented regions 512 and 514.

A dose distribution is associated with each of the spots in the arrangement 500 including the spots 501-505 and the spots 521-525. In embodiments, the spot dose distributions are normalized.

In the present example, the dose distribution of the spot 501 is compared to the dose distributions of the spots 502, 503, 504, and 505 as previously described herein. For the purposes of this example, the dose distribution for the spot 501 does not satisfy the similarly criterion. Similarly, in this example, the dose distribution of the spot 521 is compared to the dose distributions of the spots 522, 523, 524, and 525 as previously described herein, and the dose distribution for the spot 521 does not satisfy the similarly criterion. Similar comparisons are made between each of the other spots in the arrangement 500 as previously described herein.

As previously described herein, the number of spots in the regions 506 and 526 is increased, and so the spacings between spots in these regions are decreased. Dose distributions for the new spots now in those regions are then determined.

FIG. 6 illustrates an arrangement 600 of spots after spots have been added to the arrangement 500 as just described. The locations of the regions 606 and 626 correspond to the locations of regions 506 and 526, respectively. The number of spots in the regions 606 and 626 is increased relative to the number of spots in the regions 506 and 526, respectively. Consequently, the spacings between spots in the regions 606 and 626 are less than the spacings between spots in the regions 506 and 526, respectively. While the regions 606 and 626 are highlighted in this example, the number of spots can be increased in other regions throughout the target volume 510, resulting in an overall increase in the number of spots in the target volume, as shown in FIG. 6.

The process illustrated by FIGS. 5 and 6 is repeated recursively until a final arrangement 700 of spots is determined (FIG. 7). In the arrangement 700, the dose distributions of a threshold number of spots (e.g., all of the spots, or a specified number of spots) satisfy the similarity criterion, or the limit on minimum spot spacing has been reached for some or all of the spots.

Figure 8:
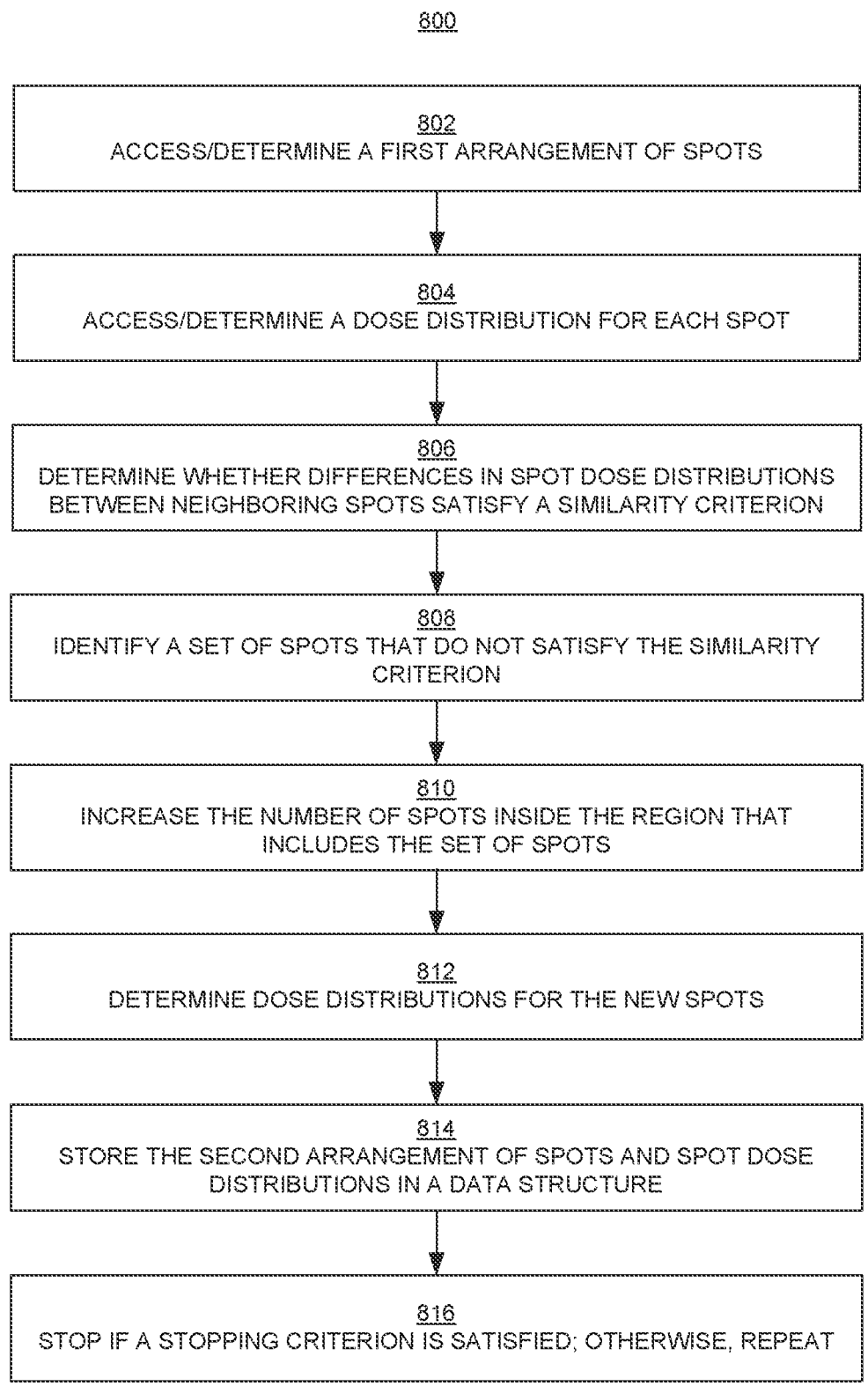
FIG. 8 is a flowchart of an example of a computer-implemented method for radiation treatment planning in embodiments according to the present disclosure.

FIG. 8 is a flowchart 800 of an example of a computer-implemented methods for radiation treatment planning in embodiments according to the present disclosure. The operations of the flowchart 800 can be implemented as computer-executable instructions (e.g., the treatment planning system 150 of FIG. 1) residing on some form of computer-readable storage medium (e.g., in memory of the computer system 100 of FIG. 1). Also, while the operations in those flowcharts are presented as occurring in series and in a certain order, the present disclosure is not so limited. The operations may be performed in a different order and/or in parallel, and they may also be performed in a recursive manner to obtain the desired result (e.g., a final arrangement of spots). FIG. 8 is discussed in conjunction with FIGS. 5, 6, and 7.

In block 802 of FIG. 8, a first arrangement 500 of spots inside a target volume 510 is accessed from computer system memory or is determined (calculated).

In block 804, a respective dose distribution for each of the spots inside the target volume 510 is accessed from computer system memory or is determined (calculated). In embodiments, the dose distributions are normalized values.

In block 806, a determination is made for each of the spots inside the target volume 510 to determine whether differences between the respective dose distribution for a spot (e.g., the spot 501 or the spot 521) and respective dose distributions for spots that are neighbors to the spot (e.g., the spots 502-505 or the spots 522-525, respectively) satisfy a similarity criterion.

In block 808, a set of spots (e.g., the spots 501-505 or the spots 521-525) that do not satisfy the similarity criterion is identified.

In block 810, the number of spots is increased inside the region of the target volume (e.g., the region 506 or the region 526) that includes locations of the sets of dissimilar spots, to produce a second arrangement of spots (e.g., the arrangement 600, the region 606 or 626) inside the target volume 510.

In block 812, a respective dose distribution is determined for each spot inside the regions 606 and 626.

In block 814, the second arrangement 600 of spots, and a respective dose distribution for each spot in the second arrangement, are stored in a data structure (e.g., the data structure 152 of FIG. 1) in computer system memory. In embodiments, the dose distributions are normalized values.

In block 816, if a stopping criterion is satisfied, then the second arrangement (and the respective dose distributions per spot) are identified as the final arrangement and stored in the data structure 152. Otherwise, the operations of the flowchart 800 are recursively repeated until a satisfactory final arrangement of spots is determined. Examples of the stopping criterion are: i) the differences between the respective dose distribution for each spot in an arrangement and respective dose distributions for spots that are neighbors to that spot satisfy the similarity criterion for a threshold number of spots (e.g., all or some of the spots), or ii) a minimum spacing limit between spots is reached.

Note that the optimization process can also be run simultaneously or asynchronously with the calculation of the data structure 152. For example, the optimization process can be started when the coarsest arrangement of spots (the initial arrangement) is accessed or determined, and then successive finer arrangements of spots can be utilized for optimization as they become available. The use of the coarser arrangement of spots is expected to be only an approximation, but it should be sufficient to get the optimization started in the right direction and thereby reduce the overall number of steps that the optimizer needs to perform. Furthermore, if the optimization converges on a satisfactory spot arrangement or if the clinical goals are met, and a successive finer arrangement of spots does not change that result, then the refinement of the data structure can be terminated before reaching the stopping criterion (such as the similarity criterion for all spots, a minimum spacing limit, or a maximum number of refinements) is satisfied.

Using the Data Structure in Optimization

As alluded to above, the data structure 152 can be used to quickly determine the influence of the dose distribution of a spot on a neighboring voxel. This capability can be especially useful for faster dose optimizations. The data structure 152 allows straightforward and efficient interpolation of the influence from an arbitrary spot to an arbitrary point (e.g., a voxel). Given a point, the influence of an arbitrary spot on the point can be interpolated using the nearest spots in the data structure. In an embodiment, a weighted average of the (normalized) dose distributions of the spots nearest to the point is used; however, more elaborate interpolation schemes can be used (e.g., a machine learning model such as a neural network). Techniques similar to image processing techniques, such as those that continuously morph one image into another image or that interpolate missing pixels from surrounding pixels, can also be applied.

Being able to efficiently calculate the dose distribution of any point allows the optimizer to vary the placements of spots and quickly determine the effects of doing so. Thus, spot positions can be varied during optimization of a treatment plan in a relatively simple and straight-forward manner that is less complicated than conventional optimization processes. For example, spots at the edge of the target volume can be moved to different points for edge enhancement, and the effect of moving the spots on the dose distribution inside the target volume can be quickly determined.

Figure 9:
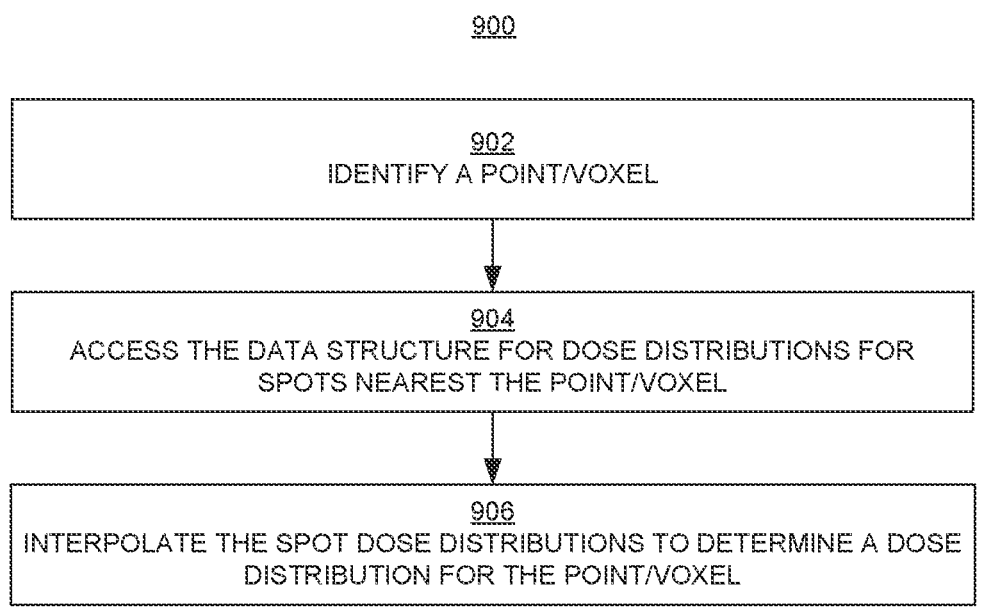
FIG. 9 is a flowchart of an example of a computer-implemented method for radiation treatment planning in embodiments according to the present disclosure.

FIG. 9 is a flowchart 900 of an example of a computer-implemented methods for radiation treatment planning in embodiments according to the present disclosure. The operations of the flowchart 900 can be implemented as computer-executable instructions (e.g., the treatment planning system 150 of FIG. 1) residing on some form of computer-readable storage medium (e.g., in memory of the computer system 100 of FIG. 1).

In block 902 of FIG. 9, with reference also to FIG. 7, a given point (e.g., the voxel 750) is identified.

In block 904, the data structure 152 (FIG. 1) is accessed. Specifically, (normalized) dose distributions for the spots (e.g., the spots 751, 752, 753, and 754) that are nearest to the voxel or point 750 are accessed from the data structure 152.

In block 906, the dose distributions for the spots 751, 752, 753, and 754 are interpolated to determine a dose distribution for the voxel or point 750. As mentioned, the interpolation can be a weighted average of the dose distributions of the spots nearest to the point, where the spot dose distributions are weighted based on the distances between the spots 751, 752, 753, and 754 and the voxel or point 750.

The spot dose normalization disclosed herein may result in unnecessarily high resolution in the data structure 152 in the beam energy direction. A solution is to not interpolate in the energy direction and to not optimize the spot locations in the energy direction. This would result in having only an energy layer-wise interpolable data structure, which would still be beneficial for optimizing the lateral penumbra.

Furthermore, because changing the beam energy during treatment is slow, completely arbitrary spot energies may lead to prohibitively long dose delivery times. An alternative would be a similarity metric and interpolation scheme that can better account for translations of features in spot dose distributions. There are well-established techniques that are used in image processing to continuously morph one image into another or to interpolate missing pixels from surrounding pixels. Those same principles could be used when interpolating between the spot dose distributions that are stored in the data structure 152.

In summary, the disclosed methodologies can provide spot locations that are conformal with the outlines of the target volume, while also providing uniform dose distributions within the target volume. Consequently, during radiation treatment, surrounding healthy tissue is spared from radiation, and dose variations within the treatment volume in general and the target volumes in particular are avoided. The methodologies disclosed herein can be particularly useful for FLASH radiation therapy in which a relatively high therapeutic radiation dose is delivered to the target within a single, short period of time. In general, use of the modeling methodologies can improve upon previous spot placement schemes.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
   a processor; and
   memory coupled to the processor and comprising instructions that, when executed, cause the processor to perform a method used for planning radiation treatment comprising spot scanning of a target volume, the method comprising:
   accessing, from the memory, a first arrangement of a plurality of spots inside the target volume;
   accessing, from the memory, a respective dose distribution for each spot of the plurality of spots inside the target volume;
   determining for said each spot whether differences between the respective dose distribution for a spot and respective dose distributions for spots that are neighbors to the spot satisfy a criterion;
   identifying a first set of spots that do not satisfy the criterion; and
   increasing a number of spots inside regions of the target volume that include locations of the first set of spots to produce a second arrangement of a plurality of spots inside the target volume.

2. The computer system of claim 1, wherein the method further comprises storing the second arrangement and a respective dose distribution for each spot of the plurality of spots of the second arrangement in a data structure in the memory.

3. The computer system of claim 1, wherein said determining comprises, for said each spot:
   determining a normalized value of the respective dose distribution for the spot; and
   determining whether differences between the normalized value for the spot and respective normalized values of respective dose distributions for spots that are neighbors to the spot satisfy the criterion.

4. The computer system of claim 1, wherein the method further comprises, after said increasing:
   determining a respective dose distribution for each spot of the spots inside the regions;
   determining, for said each spot inside the regions, whether differences between the respective dose distribution for a spot inside a region and respective dose distributions for spots inside the region that are neighbors to the spot inside the volume satisfy a criterion;
   identifying a second set of spots that do not satisfy the criterion; and
   increasing a number of spots inside regions that include locations of the second set of spots to produce a third arrangement of a plurality of spots inside the target volume.

5. The computer system of claim 4, wherein said determining, for said each spot inside the regions, comprises:
   determining a normalized value of the respective dose distribution for the spot; and
   determining whether differences between the normalized value for the spot and respective normalized values of respective dose distributions for spots that are neighbors to the spot satisfy the criterion.

6. The computer system of claim 1, wherein the method further comprises:
   determining a final arrangement of a plurality of spots inside the target volume, wherein a respective dose distribution is associated with each spot in the final arrangement, and wherein the final arrangement satisfies a condition comprising one of: i) differences between the respective dose distribution for said each spot in the final arrangement and respective dose distributions for spots that are neighbors to said each spot in the final arrangement satisfy the criterion for a threshold number of spots of the plurality of spots in the final arrangement, and ii) a minimum spacing limit is reached; and
   storing, in the memory, the final arrangement and the respective dose distribution that is associated with said each spot in the final arrangement.

7. The computer system of claim 6, wherein the method further comprises determining a dose distribution at a point between spots in the final arrangement by interpolating respective dose distributions for spots in the final arrangement that are proximate to the point.

8. The computer system of claim 6, wherein the method further comprises:
   determining a normalized value of the respective dose distribution for said each spot in the final arrangement to produce a normalized dose distribution for the target volume; and storing the final arrangement and the normalized dose distribution in a data structure in the memory.

9. The computer system of claim 8, wherein the method further comprises determining a dose distribution at a point between spots in the final arrangement by interpolating respective normalized values of respective dose distributions for spots proximate to the point.

10. The computer system of claim 9, wherein said interpolating uses a weighted average of the respective normalized values of the respective dose distributions for the spots proximate to the point.

11. A non-transitory computer-readable storage medium having computer-executable instructions for causing a computer system to perform a method used for planning radiation treatment comprising spot scanning of a target volume, the method comprising:
  accessing a respective dose distribution for each spot of a plurality of spots arranged in a first arrangement inside the target volume;
  for said each spot: determining a normalized value of the respective dose distribution for a spot; and determining whether differences between the normalized value for the spot and respective normalized values of respective dose distributions for spots that are neighbors to the spot satisfy a criterion;
  identifying a first set of spots that do not satisfy the criterion;
  determining first locations for spots inside regions of the target volume that include the first set of spots, wherein spacings between the spots inside the regions are less than spacings between spots of the plurality of spots outside the regions; and
  storing a second arrangement of spots comprising the spots inside the regions and the spots outside the regions.

12. The non-transitory computer-readable storage medium of claim 11, wherein the method further comprises:
  for each spot of the spots inside the regions: determining a respective dose distribution for a spot inside a region; determining a respective normalized value of the respective dose distribution for the spot inside the region; and determining whether differences between the respective normalized value for the spot inside the region and respective normalized values of respective dose distributions for spots that are neighbors to the spot inside the region satisfy a criterion;
  identifying a second set of spots that do not satisfy the criterion; and
  determining second locations for spots inside regions of the target volume that include the second set of spots, wherein spacings between the second locations are less than spacings between the first locations.

13. The non-transitory computer-readable storage medium of claim 11, wherein the method further comprises:
  determining a final arrangement of a plurality of spots inside the target volume, wherein a respective normalized value of a respective dose distribution is associated with each spot in the final arrangement, and wherein the final arrangement satisfies a condition comprising one of: i) differences between the respective normalized value for said each spot in the final arrangement and respective normalized values for spots that are neighbors to said each spot in the final arrangement satisfy the criterion for a threshold number of spots in the plurality of spots of the final arrangement, and ii) a minimum spacing limit is reached; and storing the final arrangement and the respective normalized value that is associated with said each spot in the final arrangement.

14. The non-transitory computer-readable storage medium of claim 13, wherein the method further comprises determining a dose distribution at a point between spots in the final arrangement by interpolating respective normalized values of respective dose distributions for spots proximate to the point.

15. The non-transitory computer-readable storage medium of claim 14, wherein said interpolating uses a weighted average of the respective normalized values of the respective dose distributions for the spots proximate to the point.

16. A computer-implemented method used for used for planning radiation treatment comprising spot scanning of a treatment volume, the method comprising:
  determining a first arrangement of a first plurality of spots inside the target volume;
  determining a respective dose distribution for each spot of the first plurality of spots;
  for said each spot: determining a normalized value of the respective dose distribution for a spot, and determining whether differences between the normalized value for the spot and respective normalized values of respective dose distributions for spots that are neighbors to the spot satisfy a similarity criterion;
  identifying a first set of spots comprising spots that do not satisfy the similarity criterion;
  determining first locations for a second plurality of spots in regions of the target volume that include the first set of spots, wherein spacings between spots of the second plurality of spots in the regions are less than spacings between spots of the first set of spots; and
  storing a second arrangement of spots comprising the spots inside the regions and spots of the first plurality of spots that are outside the regions.

17. The computer-implemented method of claim 16, further comprising:
  for each spot of the spots inside the regions: determining a respective dose distribution for a spot inside a region; determining a respective normalized value of the respective dose distribution for the spot inside the region; and determining whether differences between the respective normalized value for the spot inside the region and respective normalized values of respective dose distributions for spots inside the region that are neighbors to the spot satisfy a criterion;
  identifying a second set of spots that do not satisfy the criterion; and
  determining second locations for spots inside regions of the target volume that include the second set of spots, wherein spacings between the second locations are less than spacings between the first locations.

18. The computer-implemented method of claim 16, further comprising:
  determining a final arrangement of a plurality of spots inside the target volume, wherein a respective normalized value of a respective dose distribution is associated with each spot in the final arrangement, and wherein the final arrangement satisfies a condition comprising one of: i) differences between the respective normalized value for said each spot in the final arrangement and respective normalized values for spots that are neighbors to said each spot in the final arrangement satisfy the criterion for a threshold number of spots in the plurality of spots of the final arrangement, and ii) a minimum spacing limit is reached; and storing the final arrangement and the respective normalized value that is associated with said each spot in the final arrangement.

19. The computer-implemented method of claim 18, further comprising determining a dose distribution at a point between spots in the final arrangement by interpolating respective normalized values of respective dose distributions for spots proximate to the point.

20. The computer-implemented method of claim 19, wherein said interpolating uses a weighted average of the respective normalized values of the respective dose distributions for the spots proximate to the point.

* * * * *